United States Patent [19]

Raab

[11] 4,254,263

[45] Mar. 3, 1981

[54] PROCESS FOR PURIFYING A CYANOPYRIDINE COMPOUND

[75] Inventor: Andrew W. Raab, Pensberg, Pa.

[73] Assignee: Merck & Co., Inc., Rahway, N.J.

[21] Appl. No.: 90,791

[22] Filed: Nov. 2, 1979

[51] Int. Cl.$^3$ ............................................ C07D 213/57
[52] U.S. Cl. ....................................................... 546/288
[58] Field of Search ........................................ 546/288

[56] References Cited

U.S. PATENT DOCUMENTS 4,000,282  12/1976  Baldwin ................................ 424/263

OTHER PUBLICATIONS

March, Advanced Organic Chemistry, Sec. Ed., McGraw-Hill Pub., pp. 106–111.
Noller, Chemistry of Organic Compounds, Sec. Ed., Saunders Pub., pp. 341–344.

*Primary Examiner*—Alan L. Rotman
*Attorney, Agent, or Firm*—Daniel T. Szura; Harry E. Westlake, Jr.

[57] ABSTRACT

A process for obtaining substantially pure an alkylaminohydroxypropoxycyanopyridine from a mixture additionally containing an isomeric impurity is disclosed. The salt of the purified cyanopyridine as useful pharmaceutical activity.

9 Claims, No Drawings

PROCESS FOR PURIFYING A CYANOPYRIDINE COMPOUND

BACKGROUND OF THE INVENTION

The invention is concerned with a process for purifying an alkylaminohydroxypropoxy cyanopyridine compound.

2-(3-$C_{3-4}$alkylamino-2-hydroxypropoxy)-3-cyanopyridines are described in U.S. Pat. No. 4,000,282. The compounds have useful pharmaceutical activity. When prepared by some processes e.g. such as that exemplified in U.S. Pat. No. 4,000,282, the 2-(3-$C_{3-4}$alkylamino-2-hydroxypropoxy)-3-cyanopyridine product obtained contains as an impurity a small amount of the isomeric 2-(3-$C_{3-4}$alkylamino-1-hydroxymethylethoxy)-3-cyanopyridine. While the product cyanopyridine may be used without separating the impurity it is preferable to obtain the product cyanopyridine free from the impurity.

A process has been discovered by which said isomeric impurity is simply and directly removed from said product.

SUMMARY OF THE INVENTION

A process for obtaining (A) 2-(3-$C_{3-4}$alkylamino-2-hydroxypropoxy)-3-cyanopyridine substantially free of (B) 2-(2-$C_{3-4}$alkylamino-1-hydroxymethylethoxy)-3-cyanopyridine from a mixture containing (A) and (B) by converting (A) and (B) to their fumarate salts, separating the (A) fumarate from the (B) fumarate and recovering (A) from fumarate by conventional neutralization.

DESCRIPTION OF THE PREFERRED EMBODIMENTS

An embodiment of this invention is a process for obtaining (A) 2-(3-$C_{3-4}$alkylamino-2-hydroxypropoxy)-3-cyanopyridine substantially free of (B) 2-(2-$C_{3-4}$alkylamino-1-hydroxymethylethoxy)-3-cyanopyridine which comprises (1) treating a mixture containing (A) and (B) with fumaric acid in an alkanol liquid reaction medium, (2) separating the precipitate which forms and (3) treating said precipitate with an appropriate base, whereby compound (A) substantially free of compound (B) is obtained.

Alkanols which are useful as liquid reaction media are those having up to 3 carbon atoms. Such alkanols include methano, isopropanol and the like. A most preferred alkanol is ethanol.

In effecting the separation, at least an equivalent amount of fumaric acid is used. In other words, at least one mole of fumaric acid per two moles of cyanopyridine compound is provided. The use of greater amounts e.g. 2, 3 or 4 times the equivalent amount, is preferred. A mole ratio of fumaric acid: cyanopyridine compound of 2:11 or more is more preferred.

The amount of alkanol reaction medium used will vary and will be sufficient to permit the separation to be effected.

The separation can be illustrated by the following reaction equation sequence:

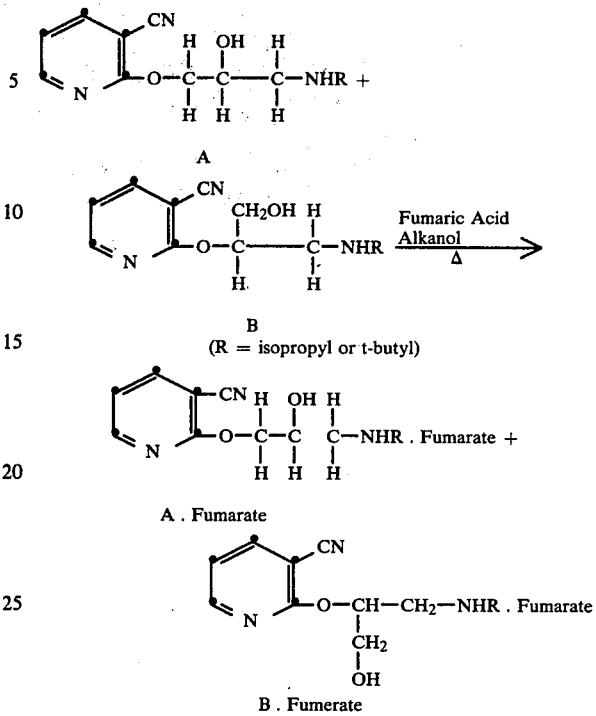

On cooling, the fumarate of B remains in solution while the fumarate of A appears as a precipitate. This precipitate can be separated by conventional means, e.g. filtration. The A fumarate can then be neutralized using conventional procedures, e.g. by treating a solution of A fumarate with a base such as NaOH, KOH, KOCH$_3$ etc. to provide the base A free of base B.

This pure product A can be converted to any pharmaceutically suitable salt e.g. hydrohalides by treatment with a soluble acid.

While the reaction equation sequence indicates that the mixture treated with fumaric acid, is free base A and B, where the A and B compounds are mixtures of salts e.g. and A HCl over the B HCl, the separation can be an integrated step by neutralizing the HCl salts and then treating the neutralized solution with fumaric acid in alkanol, without isolating the mixture of A and B bases.

The following examples illustrate the process of the present invention.

EXAMPLE 1

A. Preparation of (S) 2-phenyl-3-t-butyl-5-(3-cyano-2-pyridiyloxymethyl)oxazolidine A 5.0-liter round-bottom flask was assembled with stirrer and thermometer. One hundred grams (0.722 mole) of 2-chloro-3-cyanopyridine was charged to 1.0 liter of toluene in the flask and was rinsed in with 50 ml. of toluene. A solution of 19 g (0.037 mole) of Aliquat 336, a phase transfer catalyst, in 100 ml of toluene was added and rinsed in with 50 ml of toluene. When the contents of the flask had nearly formed a complete solution, 1.39 l of 50% aqueous sodium hydroxide was added with good agitation.

A solution of 189 g (0.804 mole, 94% pure) S-3-5-butyl-5-hydroxymethyl-2-phenyloxazolidine in 190 ml of toluene was now added at 20°-30° over 0.5 hours (cold water cooling bath) and the reaction mixture was aged another 2 hours at 25°-30° (the bath was removed; the temperature rose to 28° during the age, then dropped back to 26°). Samples were removed immediately after the oxazolidine addition and at the one and two hour age periods for G. C. assay. The reaction was essentially complete after one hour of aging.

The layers were allowed to settle over a 2-hour period and were then separated. The aqueous layer, which contained the interface, was extracted with 357 ml of toluene. The interface was then taken with the toluene extract, combined with the original toluene layer and washed with 2×400 ml of water. No interface remained after the first water wash. The toluene solution was refrigerated overnight for convenience.

B. Hydrolysis of the (A) oxazolidine

The organic layer was extracted with 2×722 ml of 1 N aqueous hydrochloric acid (the pH of the combined extracts was 0.7) the combined acid extracts were adjusted to pH 3.5 by addition of 91.3 g of solid sodium actetate. The batch was heated to 50° over 0.5 hours and held at 50° for 2.75 hours. The reaction was monitored by HPLC[1] and assays showed the reaction to be complete in 2 hours and very nearly complete in 1 hour. The final reaction pH was 3.7.

The reaction mixture was cooled to 25° and extracted with 2×300 ml of cyclohexane to remove the benzaldehyde formed during the deblocking. The aqueous layer was added to 800 ml of ethyl acetate in a 5.0-liter round-bottom flask and the pH was adjusted to 12.0 by addition of 79 ml of 50% aqueous sodium hydroxide.

The layers were separated and the aqueous portion was extracted with another 400 ml of ethyl acetate. The combined organic layer was treated with 25 g of charcoal (Calgon-PWA 20), stirred 5 minutes, then added 125 g of anhydrous sodium sulfate and stirred one hour to dry.

C. Purification via fumaric acid treatment

The batch was filtered through a pad of Supercel, the cake washed with ethyl acetate and the filtrate was concentrated in vacuo to a 160 ml. volume. The reaidue was flushed twice with 255 ml of 2B absolute ethanol (denatured with toluene), concentrating to a final volume of 145 ml after the second flush. The total volume was adjusted to 364 ml with 2B absolute ethanol and this solution was added to a solution of 42 g (0.362 mole) of fumaric acid in 885 ml of 2B absolute ethanol at 65°-75° over 10 minutes.

The batch was digested at 65°-75° for 0.5 hours and was refrigerated overnight for convenience. (an age of 0°-5° for 2 hours is satisfactory prior to filtration.) The solids were filtered, washed with 2×90 ml of cold (0°) 2B absolute ethanol and dried in vacuo at 35°. Yield, 186.4 g (84%); m.p., 216°-218°. HPLC, 99.93% pure; TLC, single spot (Rf, 0.56) plus sodium fumarate (Rf, 0.13), [CHCl$_3$/CH$_3$OH/NH$_4$OH conc. (90/10/1)-analtech GF plates visualized with UV light] $[a]_{405}^{25} = 25.5°$; E.W. 308.7 (99.6% pure); UV: A%, 411 (nm-221), 225 (nm-287).

What is claimed is:

1. A process for obtaining (A) 2-(3-C$_{3-4}$-alkylamino-2-hydroxypropoxy)-3-cyanopyridine substantially free of (B) 2-(2-C$_{3-4}$alkylamino-1-hydroxymethylethoxy)-3-cyanopyridine which comprises
   (1) treating a mixture containing (A) and (B) with fumaric acid in ethanol,
   (2) separating the precipitate which forms, and
   (3) treating said precipitate with an appropriate base, whereby compound (A) substantially free of compound (B) is obtained.

2. The process of claim 1 wherein said mixture contains less than about 29% by weight of (B).

3. The process of claim 2 wherein said base is a strong inorganic base.

4. The process of claim 3 wherein said C$_{3-4}$ alkyl group is t-butyl.

5. The process of claim 4 wherein said A compound is the S-isomer.

6. The HCl salt of the product of claim 5.

7. A process for separating 2-(3-C$_{3-4}$alkylamino-2-hydroxypropoxy)-3-cyanopyridine from a mixture additionally containing a small amount of 2-(2-C$_{3-4}$alkylamino-1-hydroxymethylethoxy)-3-cyanopyridine which comprises (1) treating the mixture with fumaric acid in alkanol and (2) separating the precipitate which forms.

8. The process of claim 7 wherein said alkanol is ethanol and said C$_{3-4}$alkyl group is 5-butyl.

9. The process of claim 8 wherein said 2-(3-t-butylamino-2-hydroxypropoxy)-3-cyanopyridine is the S-isomer.

* * * * *